United States Patent
Yu et al.

(10) Patent No.: US 11,492,597 B2
(45) Date of Patent: Nov. 8, 2022

(54) METHOD FOR ESTABLISHING COLORECTAL CANCER HK2 REPORTER GENE CELL LINE

(71) Applicant: Guangdong Medical University, Dongguan (CN)

(72) Inventors: Hongbing Yu, Dongguan (CN); Xin Liu, Dongguan (CN)

(73) Assignee: Guangdong Medical University, Dongguan (CN)

( * ) Notice: Subject to any disclaimer, the term of this patent is extended or adjusted under 35 U.S.C. 154(b) by 306 days.

(21) Appl. No.: 16/679,759

(22) Filed: Nov. 11, 2019

(65) Prior Publication Data

US 2021/0130791 A1    May 6, 2021

(30) Foreign Application Priority Data

Nov. 20, 2018   (CN) .......................... 201811384392.0

(51) Int. Cl.
*C12N 5/09*    (2010.01)
*C12Q 1/6897*  (2018.01)
*C12N 15/90*   (2006.01)

(52) U.S. Cl.
CPC ......... *C12N 5/0693* (2013.01); *C12N 15/907* (2013.01); *C12Q 1/6897* (2013.01); *C12N 2310/20* (2017.05)

(58) Field of Classification Search
CPC ............ C12N 2503/02; C12N 2510/00; C12N 2310/20; C12N 15/907; C12N 5/0693; C12Q 1/6897
See application file for complete search history.

(56) References Cited

U.S. PATENT DOCUMENTS 10,280,419 B2 *  5/2019  Tremblay ........... C07K 14/4711
2019/0106710 A1*  4/2019  Zhang ................ C12N 15/8213

OTHER PUBLICATIONS

He et al., High-Efficiency Knock-In of Large Reporter Genes in Human ESCs via CRISPR/Cas9-Induced Homology-Independent DNA Repair. Ph.D. Thesis, The Chinese University of Hong Kong, 2016, pp. 1-174. (Year: 2016).*
Szymack-Workman et al., Design and Construction of 2A Peptide-Linked Multicistronic Vectors. Cold Spring Harbor Protocols, 2012, pp. 199-204. (Year: 2012).*
Wang et al., Validation of prostate cancer risk variants by CRISPR/Cas9 mediated genome editing. bioRxiv, Sep. 17, 2018, pp. 1-25. (Year: 2018).*
Xu et al., A precision therapeutic strategy for hexokinase 1-null, hexokinase 2-positive cancers. Cancer & Metabolism., 2018, vol. 6: 7, pp. 1-17. (Year: 2018).*

* cited by examiner

*Primary Examiner* — Ganapathirama Raghu
(74) *Attorney, Agent, or Firm* — Dragon Sun Law Firm, PC; Jinggao Li; Nathaniel Perkins

(57) ABSTRACT

The present invention discloses a method for establishing a colorectal cancer HK2 reporter gene cell line, specifically including: firstly, designing a site-specific sgRNA sequence of an HK2 gene, and cloning same into a PX459 plasmid; integrating a homologous recombination sequence of an HK2 gene and a green fluorescent protein DNA fragment (EGFP), and transforming the plasmid and the integrated fragment together into a colorectal cancer cell line HCT116 by electroporation; and performing signal cell screening through a flow cytometer to obtain EGFP-expressing cells, and amplifying a monoclonal cell line; and identifying a positive HK2 reporter gene cell line through PCR identification and Western blot, among screened EGFP-expressing cell lines. The colorectal cancer cell line HK2 gene and EGFP are co-expressed, and the expression level of the EGFP is highly consistent with that of the HK2 gene. Therefore, the expression level of the HK2 gene can be accurately determined by detecting a change in the expression level of the EGFP. The method for establishing a cell line in the present invention are simple, easy to implement and efficient, and a gene site can be precisely positioned.

1 Claim, 3 Drawing Sheets

Specification includes a Sequence Listing.

METHOD FOR ESTABLISHING COLORECTAL CANCER HK2 REPORTER GENE CELL LINE

REFERENCE TO RELATED APPLICATION

This application claims the benefits of the filing dates of Chinese patent application Serial No. 201811384392.0 filed on Nov. 20, 2018, entitled "METHOD FOR ESTABLISHING COLORECTAL CANCER HK2 REPORTER GENE CELL LINE". The teachings of the entire referenced application are incorporated herein by reference.

SEQUENCE LISTING

The instant application contains an Amended Sequence Listing which has been submitted electronically in ASCII format and is hereby incorporated by reference in its entirety. Said ASCII copy, created on Jan. 22, 2021, is named "AmendedSequenceListing01222021.txt" and is 5 KB bytes in size.

TECHNICAL FIELD

The present invention relates to the field of biotechnology, and specifically, to a colorectal HK2 reporter gene cell line and an establishment method therefor.

BACKGROUND

The energy required for cell survival mainly comes from glycolysis of cytoplasm and aerobic oxidation of mitochondria. In the 1920s, Otto Warburg, a German biologist, discovered that under an aerobic condition, tumor cells may carry out glycolysis by using glucose and generate lactic acid, which is the famous Warburg effect. The research on abnormal energy metabolism of tumor cells provides a new idea for treatment of tumors. The research result of Gillies R J, et al. shows that: in normal tissues, 10% of total ATP for cell synthesis is provided by a glycolytic pathway, and the remaining 90% of the energy is provided by mitochondria; while in tumor cells, the energy provided by the glycolytic pathway accounts for 50%-70%, and the remaining energy comes from the mitochondria (Cancer and Metastasis Reviews, 2007. 26(2):311-317.2). The existing research has proved that hexokinase is the first rate-limiting key enzyme in the glycolytic pathway, and in tumor cells, Hexokinase 2 (HK2) is mainly expressed and over-expressed. The HK2 gene encodes 917 amino acids with a molecular weight of 102380 Da, and is highly conserved in mammals. A research shows that HK2 plays an important role in the process of promoting growth and proliferation of tumor cells by inhibiting apoptosis of the tumor cells, and various tumor cancer genes and cancer suppressor genes jointly regulate transcription and expression of the HK2. Wolf A, et al. proved that HK2 is over-expressed in glioblastoma, the aerobic glycolytic pathway of the cells is inhibited after the HK2 gene is knocked out, while the metabolism of an oxidative phosphorylation pathway is enhanced, and therefore, the property of increase in the expression of HK2 in the tumor cells as well as the binding of HK2 and a VDAC is one of main causes of the Warburg effect of the tumor cells (The Journal of Experimental Medicine, 2011. 208(2): 313-326). Therefore, HK2 is considered to be an important molecular target for tumor treatment for drug design and screening.

A reporter gene is an important tool in the field of molecular biology research and is generally used to mark a target gene to be studied, so that the expression level of the reporter gene is consistent with the expression level of the target gene, and thus, the expression of the target gene can be regulated by observing the expression of the reporter gene. The reporter gene has the advantages of convenience, reliability, high sensitivity, high-throughput detection and the like. At present, the commonly used reporter genes include β-galactosidase, luciferase, a fluorescent protein and the like. As non-toxic and harmless detection tools, the luciferase and the fluorescent protein occupy a dominant position in detection of cell gene expression.

CRISPR-Cas is an adaptive immune system consisting of Clustered Regularly Interspaced Short Palindromic Repeats (CRISPR) of bacteria and archaebacteria, and is used for resisting invasion of exogenous genetic materials. There is a plurality of Cas proteins which have endonuclease activity. There are three types of CRISPR-Cas systems, among which CRISPR-cas9 is the most deeply studied and most maturely applied at present; the system has the advantages of simple operation, strong flexibility in action site selection, and high activity. Under the guidance of artificially-designed sgRNA, the expressed Cas protein having the endonuclease activity may move towards the position of a gene target, and finally functions when binding to the gene target. If the integrity of a cell genome is damaged by a Cas proteinase, a self-repairing system of the cells is activated, and in the presence of an exogenous target gene with a genome homologous fragment, the cells may repair their own genome in a homologous recombination manner with a certain probability, realizing insertion of an exogenous gene.

However, at present, a rapid and efficient method for a stable cell line of a colorectal cancer HK2 reporter gene has not been established yet. This research relates to the field of colorectal cancer HK2 reporter genes, and an Enhanced Green Fluorescent Protein (EGFP)-containing colorectal cancer HK2 reporter gene cell line is established by using CRISPR-Cas9 technology, thereby providing a favorable tool for research on the HK2 gene and its signal pathway, research on pathogenic mechanisms of related diseases, and drug screening and evaluation.

SUMMARY

The first purpose of the present invention is to provide a colorectal cancer HK2 reporter gene cell line, where an HK2 gene of the cell line is linked to a downstream reporter gene through a 2A peptide to realize co-expression.

Preferably, the colorectal cancer cell is HCT116, Caco-2, SW480, SW620, LOVO, HT29 or DLD-1, further preferably HCT116.

Preferably, the reporter gene is GFP, EGFP, Luciferase or RFP.

The second purpose of the present invention is to provide a method for establishing a colorectal cancer HK2 reporter gene cell line, including the following steps:

Step 1: designing and evaluating a downstream site-specific HK2-sgRNA sequence of an HK2 gene;

Step 2: constructing a plasmid pX459/HK2-sgRNA; Step 3: integrating a homologous recombination sequence of the HK2 gene and an EGFP fragment;

Step 4: transforming the plasmid pX459/HK2-sgRNA and the integrated green fluorescent protein fragment together into a colorectal cancer cell line HCT116 by electroporation with a ratio of 1:1;

Step 5: performing single cell screening through a flow cytometer to obtain EGFP-expressing cells; and Step 6: further identifying an HK2 reporter gene cell line through genome PCR and Western blot, among screened EGFP-expressing cell lines.

Preferably, in step 1, at least two groups of HK2-sgRNA sequences, i.e., HK2-sgRNA1 and HK2-sgRNA2, are designed and screened, the sequence of the HK2-sgRNA1 is as shown in SEQ ID NO: 1, and the sequence of the HK2-sgRNA2 is as shown in SEQ ID NO: 2.

Preferably, in step 2, the method for constructing a plasmid pX459/HK2-sgRNA includes: directly obtaining a plasmid pX459/HK2-sgRNA1 or pX459/HK2-sgRNA2 with a correct sgRNA sequence after synthesizing by a biological company according to the sequence of the HK2-sgRNA1 or the sequence of the HK2-sgRNA2.

Preferably, in step 3, the method for integrating a homologous recombination sequence of the HK2 gene and an EGFP fragment includes: directly obtaining a correct integrated fragment L-EGFP-R after synthesizing by the biological company according to the homologous recombination sequence of the HK2 gene and an EGFP sequence.

Preferably, the sequence of the fragment L-EGFP-R is as shown in SEQ ID NO: 3.

The third purpose of the present invention is to provide an application of the colorectal cancer HK2 reporter gene cell line in research on tumor cell occurrence, development or energy metabolism.

Preferably, the tumor is colorectal cancer.

The fourth purpose of the present invention is to provide an application of the colorectal cancer HK2 reporter gene cell line in a cell model.

Preferably, the cell model is a tumor cell model, further preferably a colorectal cancer cell model.

The fifth purpose of the present invention is to provide an application of the colorectal cancer HK2 reporter gene cell line in research on an HK2 gene.

The sixth purpose of the present invention is to provide an application of the colorectal cancer HK2 reporter gene cell line in screening a molecules or drug for regulating the change in an HK2 gene. Preferably, the drug is an anti-cancer drug.

On the basis of conforming to common general knowledge in the art, the preferred conditions can be combined with one another to obtain specific implementation modes.

Unless specifically stated otherwise, the technology and scientific terms used in the present invention have the same meaning as understood by persons skilled in the art. The used naming methods and the described experimental methods in the present invention are widely known and are commonly used in this field.

Compared with the prior art, the present invention has the following beneficial effects.

(1) In the present invention, HK2-sgRNA capable of efficiently targeting and binding to a target site can be determined by means of hierarchical screening, and the constructed pX459/HK2-sgRNA plasmid and the integrated EGFP fragment together are directly transformed into a colorectal cancer cell line HCT116 by electroporation with a certain ratio, so that the purposes of rapidly detecting the colorectal cancer HK2 reporter gene cell having EGFP expression and establishing a stable cell line subsequently are ensured.

(2) The method in the present invention is simple, easy to implement and efficient. The well-designed and screened reporter gene is inserted into a site, and the gene site is precisely positioned by using sgRNA so as to quickly obtain the stable cell line for the target gene to be inserted, so that the method has the advantages of less time consumption and high success rate. The result shows that the EGFP knock-in efficiency reaches 7-8%. In this experiment, 7-10 strains may be screened per 96-well plate, which is significantly higher than the knock-in efficiency of generally 1% in this field. Moreover, after stable passage of 30 generations of the cell line, sequencing shows that the gene knock-in sequence still keeps genetic stability.

(3) The HK2 gene and the reporter gene EGFP are linked through a self-cleaving peptide 2A peptide to construct an operon. The self-cleaving function of the 2A peptide ensures that the HK2 gene and the EGFP can be co-expressed in cells and do not interfere with each other, thereby realizing the tracing effect of the reporter gene on the HK2 gene.

(4) The cell line in the present invention can be monitored in real time, is simple and intuitive, greatly promotes the research on related drug metabolism evaluation and related gene functions, and has clinical popularization potential and application value.

DETAILED DESCRIPTION

The present invention will be further described below in specific embodiments, so that persons skilled in the art can better understand the present invention and implement same. However, the present invention is not limited to the embodiments.

Unless otherwise specified, the experimental methods used in the following embodiments are all conventional methods, and the used materials and reagents can be obtained by commercial approaches.

Embodiment 1 Establishment of a Colorectal Cancer HK2 Reporter Gene Cell Line

In step 1, a proper HK2-sgRNA sequence is designed and evaluated:

by means of screening and evaluating, obtaining two sections of sgRNA sequences, which are respectively:

```
HK2-sgRNA1:
TAGAACCCCTGAAATCGGAA (chr2: 74890939-74890958),
as shown in SEQ ID NO: 1;
and HK2-sgRNA2:
TGTGTCAGAGACAGACCCCT (chr2: 74891015-74891034),
as shown in SEQ ID NO: 2.
```

In step 2, a plasmid pX459/HK2-sgRNA is constructed, including the following step:

directly obtaining a plasmid pX459/HK2-sgRNA1 or pX459/HK2-sgRNA2 with a correct sgRNA sequence after synthesizing by a biological company according to the sequence of the HK2-sgRNA1 or the sequence of the HK2-sgRNA2.

Figure 1:
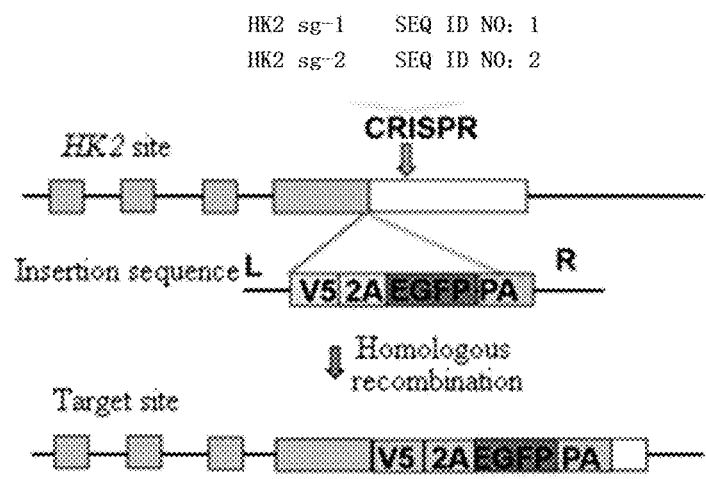
FIG. 1 is a schematic diagram of a green fluorescent protein target gene knock-in mechanism.

In step 3, an L-EGFP-R fragment is integrated, including the followings step:

directly obtaining a correct integrated fragment L-EGFP-R after synthesizing by a biological company according to a homologous arm of an HK2 gene and an EGFP sequence, where the sequence is as shown in SEQ ID NO: 3, and the construction process is as shown in FIG. 1.

In step 4, a colorectal cancer HK2 reporter gene cell line having green fluorescence is screened, including the following steps:

transforming the plasmid pX459/HK2-sgRNA and the integrated green fluorescent protein fragment L-EGFP-R together into a colorectal cancer cell line HCT116 by electroporation with a ratio of 1:1.

Figure 2:
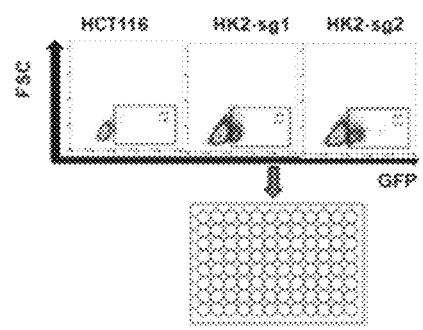
FIG. 2 is screening of a single cell clone for green fluorescent protein expression through a flow cytometer.

Firstly, single cell screening is performed with a 96-well plate through a flow cytometer (see FIG. 2), and 7-10 cell strains having EGFP expression can be obtained by each 96-well plate. The EGFP knock-in efficiency reaches 7-8%, which is significantly higher than the knock-in efficiency of generally 1% in this field.

Figure 3:
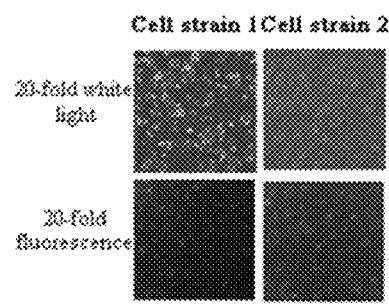
FIG. 3 is expression of a green fluorescent protein by a screened positive HK2 reporter gene cell line.

A selected monoclonal cell line is amplified and cultured (see FIG. 3). A genome DNA of cells having EGFP expression is extracted and obtained. Genome PCR is performed, and if positive amplification is obtained, it is indicated that insertion succeeds, and an HK2 reporter gene cell line is obtained. The primer sequence for PCR identification is as follows:

```
Forward primer F-GT:
GAGTCCTGGTCCTGGTCTCCC, as shown in SEQ ID NO: 4;
and

Reverse primer R-GT:
CCGAGGAGAGGGTTAGGGATAGGC, as shown in SEQ ID NO: 5.
```

Wild type cells are also subjected to the genome PCR, and the primer sequence for PCR identification is as follows:

```
Forward primer F-WT:
GAGTCCTGGTCCTGGTCTCCC, as shown in SEQ ID NO: 6;
and

Reverse primer R-WT:
GGAGAACCAATGGGAATGGTTATGATGC, as shown in SEQ ID
NO: 7.
```

Figure 4:
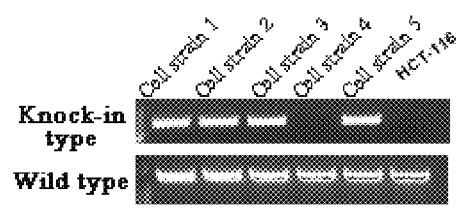
FIG. 4 is identification of an HK2 reporter gene cell line by PCR.

The comparison result of PCR identification is shown in FIG. 4, and four HK2 reporter gene cell lines are obtained.

Figure 5:
FIG. 5 is identification of an HK2 reporter gene cell line by Western blot.

Finally, a positive HK2 gene reporter cell line is further identified through Western blot, among screened EGFP-expressing cells. The identification result is shown in FIG. 5, and finally, four HK2 reporter gene cell lines are obtained.

After stable passage of 30 generations of the HK2 reporter gene cell line, sequencing shows that the gene knock-in sequence still keeps genetic stability.

Figure 6:
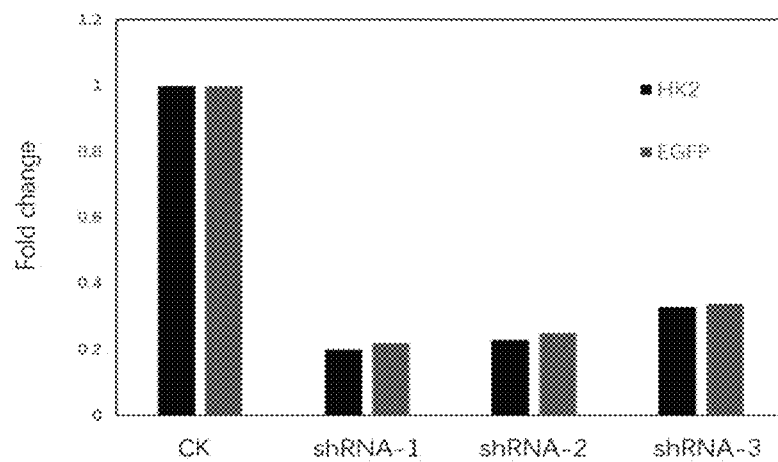
FIG. 6 is inhibition of expression of HK2 and EGFP by shRNA.

Embodiment 2 Functional Verification of a Colorectal Cancer HK2 Reporter Gene Cell Line Three different specific targeted HK2 gene small-molecule interference RNAs are designed, i.e., shRAN-1, shRAN-2, and shRAN-3, as shown in FIG. 6, which are respectively transfected into an HK2 reporter cell line. After 72 hours, according to transcriptional level analysis, it shows that compared with non-knock-down control, the three specific small-molecule interference RNAs effectively reduce the expression level of the HK2 gene (about 70-80% is knocked down). Moreover, the expression of the EGFP gene is also correspondingly reduced by 70-80% along with the knockdown of the HK2 gene. The experimental result proves from a molecular level that the reporter gene EGFP and the HK2 gene in the colorectal cancer HK2 reporter gene cell line constructed in the present invention can be synchronously co-expressed, are synchronously inhibited by shRNA, and can be used for inhibition or over-expression tracing of the HK2 gene.

Embodiment 3 Drug Screening and Evaluation Verification

Figure 7:
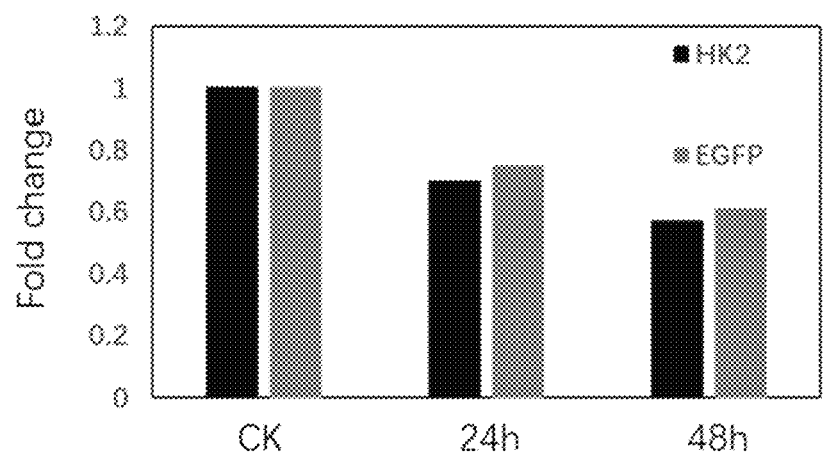
FIG. 7 is inhibition of expression of HK2 and EGFP by 2-MeOE2.

2-Methoxyestradiol (2-MeOE2) is an HIF inhibitor, and at present, has entered an anti-tumor clinical second-stage test stage. The inhibitor is used for treating the HK2 cell line, and the result shows that expression of EGFP and HK2 is inhibited, as shown in FIG. 7. The HK2 cell line is treated for 24 h or 48 h in 2-MeOE2 (10 uM), and the relative expression changes of the transcriptional level of HK2 and EGFP and those untreated as a control are analyzed. The result shows that the expression level of HK2 is obviously inhibited, and the expression of the EGFP is also synergistically inhibited. The experimental result further proves that the colorectal cancer HK2 reporter gene cell line constructed in the present invention can be used for screening and evaluating related anticancer drugs.

Finally, it should be noted that the aforementioned embodiments are only used for describing the technical solutions of the present invention rather than limiting the scope of protection of the present invention. Although the present invention has been described in detail with reference to the preferred embodiments, persons skilled in the art should understand that the technical solutions of the present invention may be modified or equivalently replaced without departing from the essence and scope of the technical solutions of the present invention.

The invention claimed is:

1. A method for establishing a colorectal cancer Hexokinase 2 reporter gene cell line, comprising the following steps:

Step 1: designing and evaluating a downstream site-specific HK2-sgRNA sequence of a Hexokinase 2 gene;

Step 2: constructing a plasmid pX459/HK2-sgRNA;

Step 3: integrating a homologous recombination sequence of the Hexokinase 2 gene and an Enhanced Green Fluorescent Protein (EGFP) fragment;

Step 4: transforming the plasmid pX459/HK2-sgRNA and the integrated green fluorescent protein fragment together into a colorectal cancer cell line HCT116 by electroporation with a ratio of 1:1;

Step 5: performing single cell screening through a flow cytometer to obtain EGFP-expressing cells, and amplifying a monoclonal cell line; and Step 6: further identifying a Hexokinase 2 reporter gene cell line through genome PCR and Western blot, among screened EGFP-expressing cell lines;

wherein in step 1, at least two groups of HK2-sgRNA sequences, HK2-sgRNA1 and HK2-sgRNA2, are designed and screened, the HK2-sgRNA1 has the nucleic acid sequence of SEQ ID NO: 1, and the HK2-sgRNA2 has the nucleic acid sequence of SEQ ID NO: 2;

wherein in step 2, the method for constructing a plasmid pX459/HK2-sgRNA comprises: directly obtaining a plasmid pX459/HK2-sgRNA1 or pX459/HK2-sgRNA2 with a correct sgRNA sequence according to the sequence of the HK2-sgRNA1 or the sequence of the HK2-sgRNA2; and wherein in step 3, the method for integrating a homologous recombination sequence of the Hexokinase 2 gene and an EGFP fragment comprises: directly obtaining a correct integrated fragment L-EGFP-R according to the homologous recombination sequence of the Hexokinase 2 gene and an EGFP sequence, wherein the fragment L-EGFP-R has the nucleic acid sequence of SEQ ID NO: 3.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial sequence
<220> FEATURE:
<223> OTHER INFORMATION: HK2-sgRNA1 Synthetic construct

<400> SEQUENCE: 1
tagaacccct gaaatcggaa          20

<210> SEQ ID NO 2
<211> LENGTH: 20
<212> TYPE: DNA
<213> ORGANISM: Artificial sequence
<220> FEATURE:
<223> OTHER INFORMATION: HK2-sgRNA2 Synthetic construct

<400> SEQUENCE: 2
tgtgtcagag acagacccct          20

<210> SEQ ID NO 3
<211> LENGTH: 2382
<212> TYPE: DNA
<213> ORGANISM: Artificial sequence
<220> FEATURE:
<223> OTHER INFORMATION: L-EGFP-R Synthetic construct

<400> SEQUENCE: 3
gagtcctggt cctggtctcc ccctccagag ttgtgctcct ctgttaggca cacttgtggc     60
ttccatggtt gttgaacttc tcttttactg actattagtt ttaagaacac agtttgccag    120
gatctcagac gtttgtccca gaattgaatc ctagctctcc taatggctga tatgatgtgg    180
aaattgggca tagtactagt gtctccaagc cacggttttc tggtacttaa taatatatag    240
taaatgttta atacattata gctgtcatcc ttctcctctt cttaattatt tctgtgtttc    300
cagcatcgct tcttagcttt catttctaag tgcaaataca aaccaatcat gactaagatg    360 gttttttcctg tgtcttcctc ccaccttttc cagctttgcc aaagtcatgc atgagacagt    420
gaaggacctg gctccgaaat gtgatgtgtc tttcctgcag tcagaggatg gcagcgggaa    480
gggggcggcg ctcatcactg ctgtggcctg ccgcatccgt gaggctggac agcgaggagg    540
taagcctatc cctaaccctc tcctcggtct cgattctacg gctagaggca gtggagaggg    600
cagaggaagt ctgctaacat gcggtgacgt cgaggagaat cctggcccag tgagcaaggg    660
cgaggagctg ttcaccgggg tggtgcccat cctggtcgag ctggacggcg acgtaaacgg    720
ccacaagttc agcgtgtccg gcgagggcga gggcgatgcc acctacggca agctgaccct    780
gaagttcatc tgcaccaccg gcaagctgcc cgtgccctgg cccaccctcg tgaccaccct    840
gacctacggc gtgcagtgct tcagccgcta ccccgaccac atgaagcagc acgacttctt    900
caagtccgcc atgcccgaag gctacgtcca ggagcgcacc atcttcttca aggacgacgg    960
caactacaag acccgcgccg aggtgaagtt cgagggcgac accctggtga accgcatcga   1020
gctgaagggc atcgacttca aggaggacgg caacatcctg gggcacaagc tggagtacaa   1080
ctacaacagc cacaacgtct atatcatggc cgacaagcag aagaacggca tcaaggtgaa   1140
cttcaagatc cgccacaaca tcgaggacgg cagcgtgcag ctcgccgacc actaccagca   1200
gaacaccccc atcggcgacg gccccgtgct gctgcccgac aaccactacc tgagcaccca   1260
gtccgccctg agcaaagacc ccaacgagaa gcgcgatcac atggtcctgc tggagttcgt   1320
gaccgccgcc gggatcactc tcggcatgga cgagctgtac aaggaattct aactagagct   1380
cgctgatcag cctcgactgt gccttctagt tgccagccat ctgttgtttg cccctccccc   1440
gtgccttcct tgaccctgga aggtgccact cccactgtcc tttcctaata aaatgaggaa   1500
attgcatcgc attgtctgag taggtgtcat tctattctgg ggggtggggt ggggcaggac   1560

```
agcaagggggg aggattggga agagaatagc aggcatgctg gggagcatca taaccattcc    1620
cattggttct cctaaaacat gaaaattatc tcccttagta atcccccttg ccaaattcca    1680
tgtccctgta taattctaca ggatggggac actaatgaag atacggttgc ttcaccttgg    1740
agcctgaaca tgacatttct aagtggggtg catcccccag cactgatgtt gttactgatt    1800
ctcctgtcag agatctggga ggtctccact gaggatgtga gcctgattat cctataggca    1860
gacgtgggga gggtggaggg gtgacagtgg aggaaaatcc tggatatcca cgcagcagcc    1920
cctctttaac ctcatctaca agcatttgcc ctgtggattc cagcatttgc cattcctgga    1980
atcaaggaat cctgagtctg ggcaatgaaa ccaaagccag gagttgacgc atcctgcagt    2040
tgggccagct gtcgcatctc agcggggcgc acatgttatc cacaagcaat ggacctttgg    2100 ggaagggggga gttttagtt tgttttacaa attttcctg caaaagtgga atcactgtat    2160
tttcatttta atttataattt gaaattttat ttagttcttg agtagatctg cttcttcatc    2220
ttgacatgta atgaatggtc agttgtacgt aatgtattta tatgttaatt tgttatgtat    2280
atagatgtgc aagtcttgtc agaattggcc tcagtgtagt taaagggcag aaggggaaga    2340
tactgactag tcatagaaat acctcattcg cctgtgggaa ga                      2382
```

```
<210> SEQ ID NO 4
<211> LENGTH: 21
<212> TYPE: DNA
<213> ORGANISM: Artificial sequence
<220> FEATURE:
<223> OTHER INFORMATION: F-GT Synthetic construct

<400> SEQUENCE: 4
gagtcctggt cctggtctcc c                                              21

<210> SEQ ID NO 5
<211> LENGTH: 24
<212> TYPE: DNA
<213> ORGANISM: Artificial sequence
<220> FEATURE:
<223> OTHER INFORMATION: R-GT Synthetic construct

<400> SEQUENCE: 5
ccgaggagag ggttagggat aggc                                           24

<210> SEQ ID NO 6
<211> LENGTH: 21
<212> TYPE: DNA
<213> ORGANISM: Artificial sequence
<220> FEATURE:
<223> OTHER INFORMATION: F-WT Synthetic construct

<400> SEQUENCE: 6
gagtcctggt cctggtctcc c                                              21

<210> SEQ ID NO 7
<211> LENGTH: 28
<212> TYPE: DNA
<213> ORGANISM: Artificial sequence
<220> FEATURE:
<223> OTHER INFORMATION: R-WT Synthetic construct

<400> SEQUENCE: 7
ggagaaccaa tgggaatggt tatgatgc                                       28
```